United States Patent
Baker et al.

(10) Patent No.: US 12,115,362 B2
(45) Date of Patent: *Oct. 15, 2024

(54) MICROCARTRIDGE

(71) Applicant: NOBLE INTERNATIONAL, INC., Orlando, FL (US)

(72) Inventors: Jeff Baker, Orlando, FL (US); Francis Michael Siemer, Orlando, FL (US); Christopher Chung, Orlando, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 52 days.

This patent is subject to a terminal disclaimer.

(21) Appl. No.: 16/404,545

(22) Filed: May 6, 2019

(65) Prior Publication Data

US 2019/0321563 A1 Oct. 24, 2019

Related U.S. Application Data

(63) Continuation of application No. 14/872,674, filed on Oct. 1, 2015, now Pat. No. 10,279,123.

(51) Int. Cl.
*A61M 5/32* (2006.01)
*A61M 5/315* (2006.01)
(Continued)

(52) U.S. Cl.
CPC ...... *A61M 5/3275* (2013.01); *A61M 5/31501* (2013.01); *A61M 5/3202* (2013.01);
(Continued)

(58) Field of Classification Search
CPC .. A61M 5/20; A61M 5/2033; A61M 5/31501; A61M 5/31505; A61M 5/3202;
(Continued)

(56) References Cited

U.S. PATENT DOCUMENTS 5,057,087 A * 10/1991 Harmon ............... A61M 5/3243
604/198
5,263,934 A * 11/1993 Haak .................... A61M 5/322
604/110
(Continued)

FOREIGN PATENT DOCUMENTS

WO   WO-03097133 A1 * 11/2003 .......... A61M 5/2033
WO   2006000785 A1    1/2006

OTHER PUBLICATIONS

Extended European Search Report in European Application No. 16852849.5, mailed Apr. 24, 2019.
(Continued)

*Primary Examiner* — Shefali D Patel
(74) *Attorney, Agent, or Firm* — Timothy H. Van Dyke; Wolter, Van Dyke, Davis, PLLC

(57) ABSTRACT

A container for delivering a medicament to a target location includes a housing having a proximal end and a distal end, the housing including a cap locking tab at the distal end, and a vial containing the medicament. The container includes a plunger slidable within the vial from a proximal end to a distal end of the vial to dispel the medicament, an injection member associated with the distal end of the vial, such that the medicament dispelled from the vial passes through the injection member to the target location, and a slidable interaction member associated with the distal end of the vial configured to slide with the vial. An interaction between the slidable interaction member and the cap locking tab causes the cap locking tab to bias outward, and placement of a safety cap on the container after use locks the safety cap onto the container via an interaction with the cap locking tab. The container may further include a resistance feature to control movement of a plunger rod relative to the vial.

6 Claims, 5 Drawing Sheets

(51) Int. Cl.
*A61M 5/50* (2006.01)
*A61M 5/20* (2006.01)
*A61M 5/46* (2006.01)

(52) U.S. Cl.
CPC .......... *A61M 5/3213* (2013.01); *A61M 5/322* (2013.01); *A61M 5/3221* (2013.01); *A61M 5/3232* (2013.01); *A61M 5/3245* (2013.01); *A61M 5/502* (2013.01); *A61M 5/5086* (2013.01); *A61M 2005/2086* (2013.01); *A61M 2005/31508* (2013.01); *A61M 2005/3151* (2013.01); *A61M 5/31511* (2013.01); *A61M 5/3204* (2013.01); *A61M 2005/3247* (2013.01); *A61M 5/326* (2013.01); *A61M 5/46* (2013.01); *A61M 2005/5033* (2013.01); *A61M 2205/583* (2013.01); *A61M 2205/59* (2013.01)

(58) Field of Classification Search
CPC .. A61M 5/3205; A61M 5/321; A61M 5/3213; A61M 5/322; A61M 5/3221; A61M 5/3232; A61M 5/3234; A61M 5/502; A61M 5/5086; A61M 2005/2026; A61M 2005/2086; A61M 2005/3143; A61M 2005/31506; A61M 2005/31508; A61M 2005/5033; A61M 2205/273; A61M 2205/583; A61M 5/315; A61M 5/31511; A61M 5/31515; A61M 5/32; A61M 5/3204; A61M 5/3243; A61M 5/3245; A61M 5/326; A61M 5/3275; A61M 5/46; A61M 5/50; A61M 2005/3151; A61M 2005/3247; A61M 2205/27
See application file for complete search history.

(56) References Cited

U.S. PATENT DOCUMENTS

| | | |
|---|---|---|
| 2004/0193110 A1 | 9/2004 | Giambattista et al. |
| 2004/0236284 A1* | 11/2004 | Hoste .................... A61M 5/326 604/198 |
| 2005/0171477 A1 | 8/2005 | Rubin et al. |
| 2007/0265568 A1 | 11/2007 | Tsals et al. |
| 2009/0312703 A1 | 12/2009 | Pickhard |
| 2011/0319864 A1 | 12/2011 | Beller et al. |
| 2012/0046613 A1* | 2/2012 | Plumptre ........... A61M 5/31511 604/189 |
| 2013/0317480 A1 | 11/2013 | Reber et al. |

OTHER PUBLICATIONS

International Search Report and Written Opinion in International Application No. PCT/US2016/055219, mailed Feb. 3, 2017.
Supplementary European Search Report in European Application No. 16852849.5, mailed Apr. 24, 2019; 6 pages.

* cited by examiner

MICROCARTRIDGE

CROSS-REFERENCE TO RELATED APPLICATIONS

This application is a continuation application of U.S. application Ser. No. 14/872,674 filed Oct. 1, 2015, which is incorporated by reference herein.

BACKGROUND

Injection devices are used for administering medications via a needle. Certain disease states require those suffering from them to receive injections often. Those suffering from diabetes, for example, require frequent administration of injections, which are typically self-administered often in a non-clinical setting. Injection devices including auto-injectors or prefilled syringe injection devices are typically used to self-administer injections and most of these devices are single-use injection devices in order to minimize the risk of infections associated with re-use of the injection device by the same or a different user. Reducing accidental needle stick injuries caused by contaminated needles is also a concern. Therefore, a need exists for the prevention of re-using needles and/or injection devices, as well as prevention of accidental needle-sticks by users of injection devices.

SUMMARY

In one embodiment, a container for delivering a medicament to a target location is provided. The container including a housing having a proximal end and a distal end, the housing including a cap locking tab at the distal end, the container further including a vial having a proximal end and a distal end, the vial configured to contain a medicament, the vial being movable relative to the housing. The container further includes a plunger associated with the proximal end of the vial, the plunger configured to slide within the vial from the proximal end to the distal end of the vial to dispel the medicament from the vial. The plunger may be associated with a plunger rod configured to interact with the plunger. The container may further include an injection member associated with the distal end of the vial, such that medicament dispelled from the vial passes through the injection member to the target location. A slidable interaction member is associated with the distal end of the vial, the slidable interaction member configured to slide with the vial; and a safety cap including a cap groove, the safety cap configured to interact with the distal end of the housing. Moving the vial toward the distal end of the housing causes the slidable interaction member to interact with the cap locking tab, biasing the cap locking tab outward, such that adjoining the safety cap to the distal end of the housing causes the cap groove to interact with the cap locking tab, preventing removal of the safety cap after use of the container.

In a further embodiment, a method of injecting medicament into a subject is provided. The method includes obtaining a container for delivering a medicament to a target location. The method further includes applying the distal end of the container to a target area on the subject and depressing the plunger rod to insert the injection member and deliver the medicament. In a further embodiment, the method may include releasing the plunger rod to allow retraction of the injection member, wherein upon retraction, the injection member is locked within the housing. In still a further embodiment, the method may include removing the safety cap prior to the applying step. In yet a further embodiment, the method may include attaching the safety cap subsequent to the releasing step, whereby the safety cap is permanently locked.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 2A is a is a cross sectional view of another embodiment of a container for delivering a medicament to a target location with a safety cap on.

FIG. 2B is a cross sectional view of the embodiment of FIG. 2A, following removal of the safety cap.

FIG. 2C is a cross sectional view of FIG. 2B following activation of the container by actuation of the plunger and delivery of the injection member.

FIG. 2D is a cross sectional view of the container of FIG. 2C following deliver of medicament from the container.

FIG. 2E is a cross sectional view of the container of FIG. 2D following retraction of the injection member.

DETAILED DESCRIPTION

Figure 1:
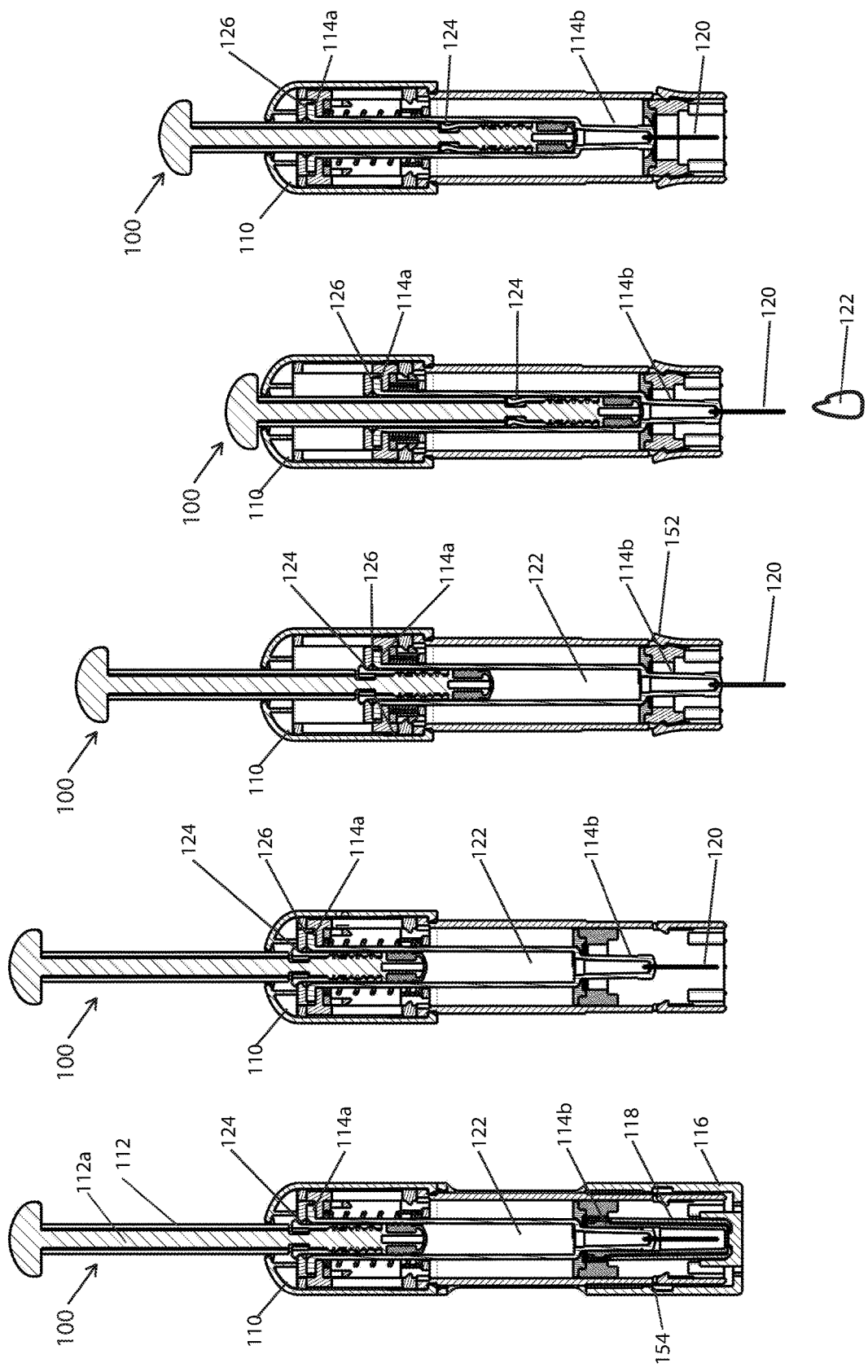
FIG. 1A is a cross sectional view of a further embodiment of a container for delivering a medicament to a target location with a safety cap on the distal end of the container.
FIG. 1B is a cross sectional view of the embodiment of FIG. 1A, following removal of the safety cap.
FIG. 1C is a cross sectional view of FIG. 1B following application of a force on the plunger rod, movement of the vial, and delivery of the injection member.
FIG. 1D is a cross sectional view of the container of FIG. 1C following biasing inward of the flexible tabs on the plunger rod and delivery of medicament.
FIG. 1E is a cross sectional view of the container of FIG. 1D following use of the container and retraction of the injection member.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including." "includes," "having." "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

The term "adjacent" as used herein, includes but is not limited to near, associated with, or in close proximity to.

The term "threshold resistance force" as used herein, includes but is not limited to a force required to initiate movement of a plunger rod relative to a vial. In an embodiment, it is the force at which the flexible tabs relieve to initiate movement of the plunger rod relative to the vial. The "threshold" may be adjustable based on variables including, but not limited to, type of medicament, amount of force required of the biasing member, contact and interactivity between various components of the container including friction between the plunger and the inner surface of the vial, and relative movement there between, and other variables known to those skilled in the art.

The inventors herein have identified a need for an injection device with features for safety both before and after use as well as additional features for ease of use of the device.

FIGS. 1A-1E include cross sectional sequential views showing the use of the container embodiment 100 including a housing 110 with a vial 114 including a proximal and distal vial end 114a, 114b, respectively, the vial 114 for housing a medicament 122. The container 100 further includes a plunger 112 comprising a plunger rod 112a and an injection member 120 extending from the distal end of the housing 110, wherein the injection member 120 is configured to deliver medicament 122 to a target site of a subject. The container embodiment 100 further includes a safety cap 116 comprising a cap groove 154. The safety cap 116 being configured to include or receive an injection member cover 118 there within. When the safety cap 116 is placed over a distal end of the housing 110, the injection member cover 118 is configured to cover at least a portion of the injection member 120.

In one embodiment, a resistance member is shown as flexible tabs 124 disposed on the plunger rod 112a, and a plunger adaptor component 126 is further provided for interfacing with the tabs 124, to account for tolerances in manufacturing in one non-limiting example. The plunger adaptor component 126 can be formed of a deformable material, in some non-limiting embodiments, to account for different spaces and dimensions that may occur during manufacturing. In some non-limiting embodiments, the plunger adaptor component 126 may include a spacer, a bushing, a hat bushing, or any other similar type of component known to those skilled in the art. In another non-limiting embodiment, in some instances, the plunger adaptor component 126 may limit or prevent rotation of the vial 114 or the housing 110 as either the vial and/or the housing move.

Moreover, the tabs 124, which interface with the plunger rod 122 and, in one non-limiting embodiment, with the plunger adaptor component 126, provide a resistance on the movement of the plunger 112 relative to the vial 114. The tabs 124 provide a resistance on the movement of the plunger 112 such that application of a distal force to the plunger rod 112a causes the vial 114 to move toward the distal end of the housing 110 to deliver the injection member 120, and upon reaching a threshold resistance force via the at least one resistance feature (for example, tabs 124) the plunger rod 112a slides within the vial 114 toward the distal end of the vial 114b to deliver the medicament 122 contained there within. The at least one resistance feature (for example, tabs 124) causes delivery of the injection member 120 from the housing 110 prior to delivery of the medicament 122 through the injection member 120.

Figure 4:
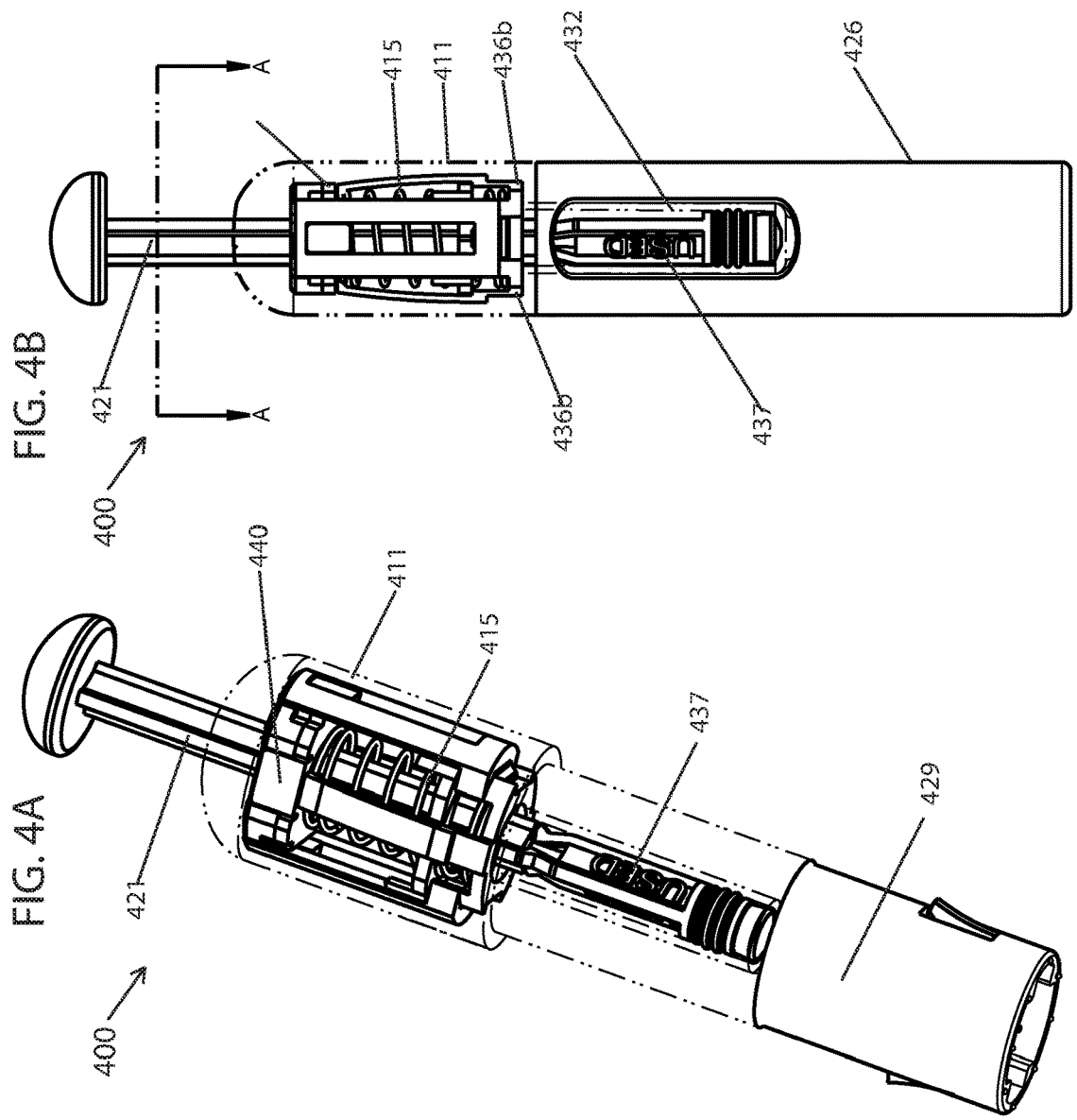
FIG. 4A is a perspective view of an embodiment of a container following retraction of the injection member.
FIG. 4B is a perspective view of the embodiment of the container of FIG. 4A following retraction of the injection member and replacement of the safety cap in a locked position.
FIG. 4C is a cross sectional view of an embodiment of the plunger rod taken at line A-A of FIG. 4B.

While in some non-limiting embodiments provided herein, the at least one resistance feature is shown by flexible tabs on the plunger rod, other possible embodiments of the resistance feature may be provided. The resistance feature of the plunger is configured such that it allows the plunger rod to slide within the vial once the threshold resistance force is met. Other embodiments of this feature may include a telescoping In FIGS. 2A-C movement of the plunger rod 23 toward the distal end of the housing 10' causes the at least one flexible tab 41 to press against the vial 14, a biasing member 15 disposed within the housing is compressed as seen in FIG. 4C, and the vial 14 to move toward the distal end of the housing 10' delivering the injection member 20 as shown in FIG. 4C. Further movement of the plunger rod 23 toward the distal end of the housing 10' as shown in FIG. 4D, causes the at least one flexible tab 41 to flex inward toward the plunger rod 23, and the plunger rod 23 to slide further within the vial 14 toward the distal end of the vial 14 to deliver medicament there within. Following deliver of medicament in FIG. 4D, the vial 14 and injection member 20 is retracted back into the housing 10' by release of the biasing member 15.

Figure 5:
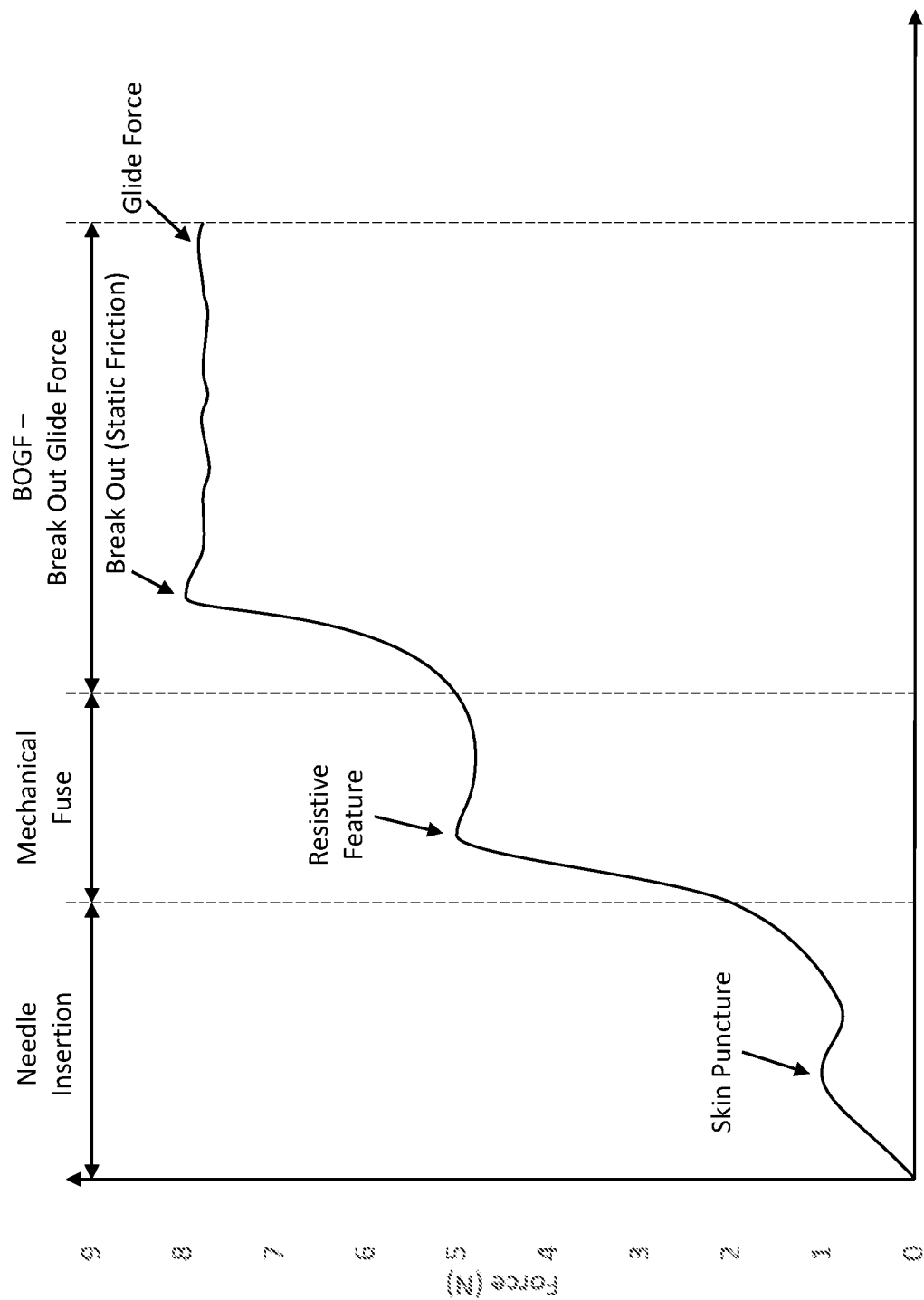
FIG. 5 includes a graphical illustration of the various forces encountered during use of the container embodiments described herein.

FIG. 5 includes a graphical illustration of the various forces encountered during use of the container embodiments described herein. The graph provides a force (N) on the x-axis versus phase of operation on the y-axis, providing an analysis of insertion force, mechanical fuse force, and break out glide force (BOGF). These are the forces encountered during use of the container embodiments. During a typical injection, a user encounters various forces including an insertion force, followed by a break out glide force. There is typically a rapid transition between these forces. The break out force is the threshold for initial movement and is based on the static friction between the stopper and the vial. The glide force is the resistance force to movement of the plunger and is based on the dynamic friction between the stopper and vial. The insertion force typically ranges from 1-2 N (Newtons) and accounts for the force to insert a needle into the skin, the BOGF typically occurs at 5-8 N or more, which is the force required to deliver the medicament through the injection member and into the user. If the plunger were to move too soon in the cycle, medicament would be expelled before the needle is at the proper depth. By adding a transitioning step from a mechanical fuse feature that is more precisely controlled that the interference between the rubber stopper and the vial, the device would be more repeatable as to not dispel medicament before the correct needle depth is reached. Consequently, the container embodiments described herein provide a transition between these forces, i.e., a 3-5N mechanical fuse force that is required between the insertion force and the BOGF to control the transition between these two typically encountered forces. The embodiments described herein provide components which interact with one another to govern and smooth this transition, and to ensure that the injection member has been fully inserted into the skin of the user before the medicament is delivered from the container through the injection member.

The one or more plunger adaptors as described herein include components that may be used to account for tolerances in manufacturing. These adaptors provide contact between the flexible tabs and the vial, whether or not the components of the device are made the same size in all devices in manufacturing, in some examples. In some non-limiting embodiments, the one or more plunger adaptors may include a pliable material. The plunger adaptors may control radial dimensions of the container. In other non-limiting embodiments, the plunger adaptor may prevent rotation of the vial as it moves relative to the container. The plunger adaptors can be one or more and may include a ring like structure or other structure.

In a non-limiting embodiment, the term cap groove, as used herein, includes but is not limited to a groove in the safety cap that interacts with a cap locking tab on the distal portion of the container, or in another, non-limiting embodiment, the groove may be on the distal end of the container, and the cap locking tab may be on the inner surface of the safety cap, such that an interaction between the two would accomplish the task of preventing the cap from being removed from the container after use of the container due to the interaction between the cap locking tab and the cap groove. In one embodiment, the groove may only partially extend into the wall of the safety cap as shown in FIGS. 1A-E, in another non-limiting embodiment, the groove may include an opening which fully extends through the wall of the safety cap, in yet another embodiment the cap groove may include a cut through or recess, or any other type of structure partially or fully extending through the wall of the cap to create resistance between or to provide interaction between the cap locking tab and the cap groove.

A slidable interaction member 184 may be associated with the distal end of the vial 114b in some non-limiting embodiments. The slidable interaction member 184 is configured to slide with the vial 114; and a safety cap 116 including a cap groove 154, the safety cap 116 configured to interact with the distal end of the housing 110. Actuation of the plunger 112 by moving the plunger 112 toward the distal end of the housing 110 moves the vial 114 toward the distal end of the housing 110, (in embodiments where a plunger rod 112a is associated with the plunger 112, this can be done by actuating the plunger rod 112a, which in turn, actuates the plunger 112. This action biases the biasing member 115, and causes the injection member 120 to traverse the target surface 122. Moving the vial 114 toward the distal end of the housing 110 causes the slidable interaction member 184 to interact with the cap locking tab 152, biasing the cap locking tab 152 outward, such that later adjoining the safety cap 116 to the distal end of the housing 110 causes the cap groove 154 of the safety cap 116 to interact with the cap locking tab 152, thereby preventing removal of the safety cap 116 after use of the container 100, see FIG. 1D, FIG. 1G.

Further, movement of the plunger 112 toward the distal end of the housing 110 causes the plunger 112 to slide relative to the vial 114 toward the distal end 114b, such that medicament 122 within the vial 114 is delivered through the injection member 120 as shown in FIG. 1D. Release of the pressure against the plunger 112 and/or the plunger rod 112a causes release of the biasing member 115 as shown in FIG. 1E, so as to retract the injection member 120 into the housing 120 as the vial 114 moves toward the proximal end of the housing 120. Adjoining the safety cap 116 onto the distal end of the housing 110 causes the cap groove 154 to interact with the cap locking tab 152, such that the safety cap is in a locked position, preventing removal of the safety cap after use of the container 100.

The safety cap 116 may further include an injection member cover 118 there within as shown in FIG. 1A, configured to surround the injection member 120 when the safety cap 116 is adjoined to the distal end 110b of the housing 110. The safety cap 116 and/or the injection member cover 118 may be provided to maintain sterility of the injection member 120 prior to use of the container 100, and to provide protection from accidental needle sticks to a user via the injection member 120 prior to and following injection. In some, non-limiting embodiments, at least a portion of the housing may include a viewing window 432 providing a view into the housing (shown in FIGS. 3A-3C).

In a further non-limiting embodiment, the plunger rod 112a may include a plunger contact member at the proximal plunger rod end which may be formed of a material to enhance the gripping contact between the user and the plunger contact member and prevent slipping during use. The material may include a rubber material in one non-limiting embodiment. Other similar materials known to those skilled in the art may be used to prevent slipping. Further, an etched or other irregular surface may be included on the plunger contact member in place of, or in addition to the rubber material, to increase and maintain contact between the user and the plunger contact member during use of the container 100. In non-limiting embodiments, the rubber material provides a more secure grip to a user; the shape and size of the plunger contact member can vary to provide a flatter portion for better grip, or another user friendly shape to enhance the injection experience and reduce slipping off of the plunger contact member during use.

FIGS. 2A-E provide sequential cross-sectional views of a container embodiment 200 for delivering a medicament to a target location, including a housing 210 having a proximal end and a distal end, a vial 214 having a proximal end 214a and a distal end 214b, the vial 214 configured to contain a medicament in some non-limiting embodiments. The vial 214 configured to move relative to the housing 210. An injection member 220 associated with the distal end of the vial 214b, such that medicament delivered from the vial 214 passes through the injection member 220 to the target location. The container embodiment 200 further includes a plunger 218 slidable within the vial 214 from the proximal end to the distal end of the vial 214 to dispel the medicament from the vial 214 or to simulate movement of a plunger 218 in a medicament delivery device, in an alternative embodiment. A plunger rod 223 having a proximal end and a distal end, the distal end of the plunger rod associated with the plunger, said plunger rod 223 being slidable relative to the vial 214. Application of a force to the plunger rod causes the vial 214 to move toward the distal end of the housing delivering the injection member 220, upon reaching a threshold resistance force wherein at least one resistance feature associated with the plunger rod 223 allows the plunger rod 223 to slide within the vial 214 toward the distal end of the vial to deliver the medicament.

In one, non-limiting embodiment shown in FIGS. 2A-2E, the at least one resistance feature may include at least one flexible tab 241 associated with a portion of the plunger rod 223, configured to interact with the proximal end of the vial 214. The plunger rod 223 and plunger 218 are shown as connected or one continuous component, in the embodiment shown in FIGS. 2A-E, and in some alternative embodiments, these components may be separate and distinct from one another as shown in an embodiment provided in FIGS. 3A-3F wherein prior to actuation of the plunger rod 223, a space is disposed between the two components.

Figure 2:
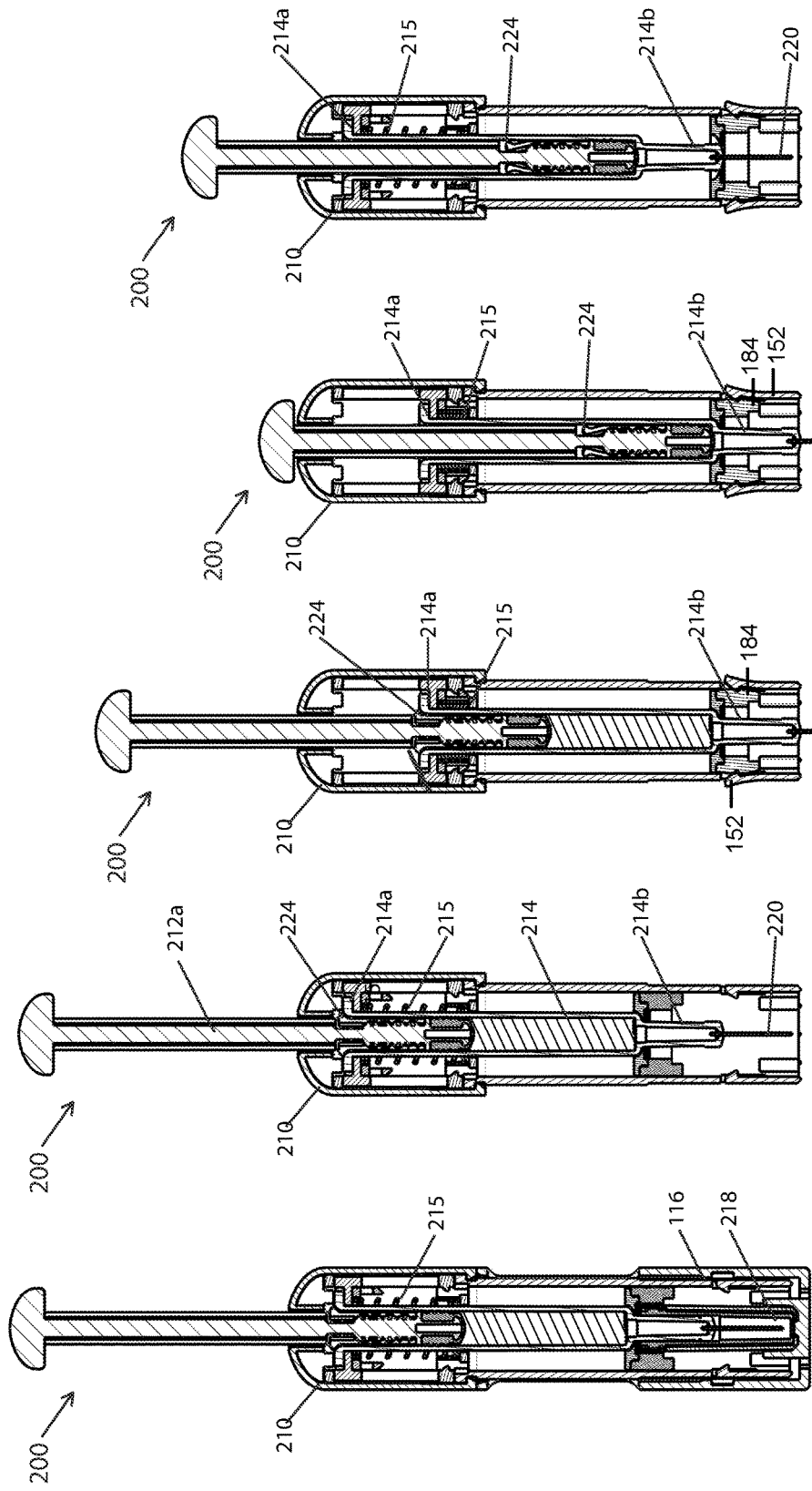

In FIGS. 2A-C movement of the plunger rod 223 toward the distal end of the housing 210 causes the at least one flexible tab 241 to press against the vial 214, a biasing member 215 disposed within the housing is compressed as seen in FIG. 2C, and the vial 214 to move toward the distal end of the housing 210 delivering the injection member 220 as shown in FIG. 2C. Further movement of the plunger rod 223 toward the distal end of the housing 210 as shown in FIG. 2D, causes the at least one flexible tab 241 to flex inward toward the plunger rod 223, and the plunger rod 223 to slide further within the vial 214 toward the distal end of the vial 214 to deliver medicament there within. Following delivery of medicament in FIG. 2D, the vial 214 and injection member 220 is retracted back into the housing 210 by release of the biasing member 215.

Figure 3:
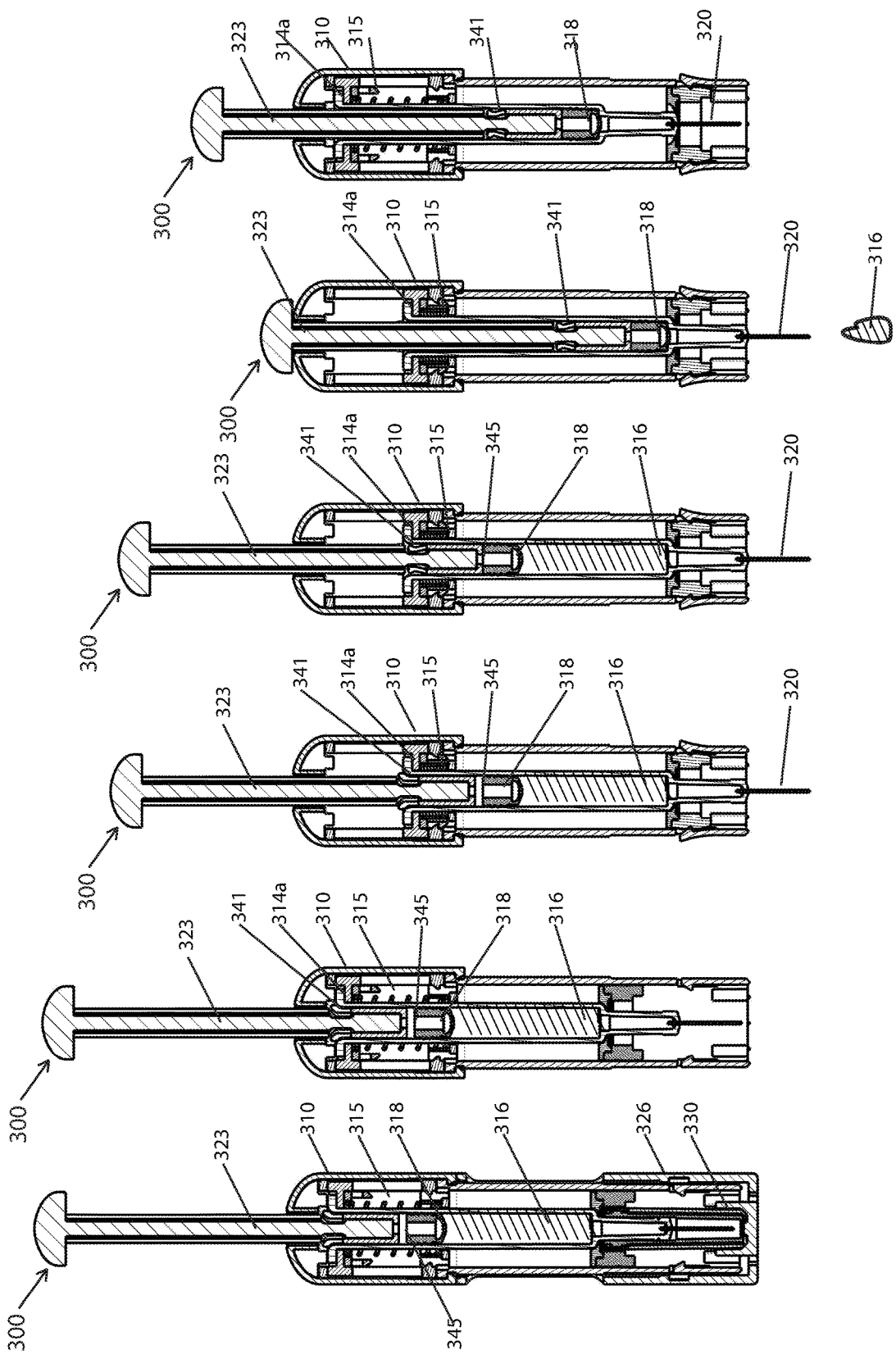
FIG. 3A is a cross sectional view of a further embodiment of a container for delivering a medicament to a target location with a safety cap on the distal end of the container.
FIG. 3B is a cross sectional view of the embodiment of FIG. 3A, following removal of the safety cap.
FIG. 3C is a cross sectional view of FIG. 3B following application of a force on the plunger rod, and delivery of the injection member.
FIG. 3D is a cross sectional view of the container of FIG. 3C following biasing inward of the flexible tabs on the plunger rod.
FIG. 3E is a cross sectional view of the container of FIG. 3D following delivery of the medicament.
FIG. 3F is a cross sectional view of the container of FIG. 3E following use of the container and retraction of the injection member.

FIGS. 3A-3F show a cross-sectional container embodiment 300 wherein a gap 345 is provided between the plunger 318 and the plunger rod 323. During use, as a force is exerted on the plunger rod 23, a biasing member 315 is compressed, the vial 314 moves toward the distal end of the housing as shown in FIG. 3C to deliver the injection member 320 from the housing. The flexible tabs 341 remain in contact with the proximal end of the vial 314, and the gap 345 remains between the plunger 318 and the plunger rod 323. Once the vial 314 has reached the distal end of the housing 310 and the injection member 320 is fully extended, additional force on the plunger rod 323 causes the flexible tabs 341 to move inward as shown in FIG. 3D, and a distal end of the plunger rod 323 to contact the plunger 318 removing the gap there between. Continued force on the plunger rod 323 causes the vial 314 to move toward the distal end of the housing 310 and causes the medicament 316 contained within the vial to be delivered from the device (FIG. 3E). This gap 345 provides, in one embodiment, an additional means of preventing delivery of medicament 316 through the injection member 320 until the injection member 320 is inserted into the target area to a target depth. Following use of the container embodiment 300, the biasing member 315 extends, retracting the vial 314 and the injection member 320 into the housing 310.

In this non-limiting embodiment as shown in FIGS. 4A-C, a container 400 may include a plunger rod 421 having a triangular shaped body as shown in FIGS. 4A-4C. A visual indicator 437, may be provided on one or more of the first surface 421c, second surface 421b or third surface 421d of the plunger rod 421 triangular body. The visual indicator 437 may provide a status of use to the user of the container 400. For example, prior to use, the visual indicator 437 may not be shown (i.e., it may be hidden under another component of the container 400, or a portion of the housing that is non-transparent, i.e., opaque in a non-limiting example) and following use or during use of the container 400 (i.e., after actuation of the plunger 418), the visual indicator may be shown, in a non-limiting embodiment. In one embodiment, as shown in FIGS. 4A-4C, the visual indicator 437 may include the word USED, such that it can be used to communicate to a user that the container 400 has been used, and in this embodiment, the USED visual indicator 437 may only be readable once an injection with the container has completed. Therefore, the visual indicator 437 may appear within a viewing window 432 of the container such that a user may view the visual indicator 437 only after having used the container. This feature is beneficial in preventing multiple uses of a used device and/or preventing unwanted needle-sticks with a used container 400.

In a non-limiting embodiment, the housing may include a non-transparent portion to prevent a user from viewing the injection member during use of the container 400. The term "non-transparent" as used herein includes, but is not limited to, opaque, translucent, and may include at least a portion of the housing having one or more of these features which may occur by use of a material encompassing these features, or with a finish on the container, a surface treatment, a paint, and also further includes a label which may prevent a user from viewing the injection member during the course of using the container 400.

FIGS. 4A-4C show a non-transparent region 429 of the housing adjacent to the injection member, wherein the non-transparent region 429 prevents a view of the injection member 420 by the user during use of the container 400 to decrease user-anxiety associated with the handling of injection members 420, i.e., needles.

In a further embodiment, the plunger rod 421 comprises a triangular body comprising a first surface 421c, a second surface 421d and a third surface 421e, in one non-limiting embodiment shown in FIG. 4C. The visual indicator 437 may be visible from any angle by the user due to the triangular shaped body of the plunger rod 421. FIG. 4C provides a cross-sectional view of the plunger rod 421 taken at line A-A in FIG. 4B.

Features of the embodiments described herein, including the viewing window, triangular rod with/without visual indicator, e.g. USED indicator, pictorial IFU, rubber contact on plunger rod, or other such features, may be included on any of the embodiments described herein and may be independently combinable, and are not required on any embodiments described herein.

In one embodiment, a method of injecting medicament into a subject is provided. The method includes obtaining a container for delivering a medicament to a target location. The container including a housing having a proximal end and a distal end, the housing including a cap locking tab at the distal end, the container further including a vial having a proximal end and a distal end, the vial configured to contain a medicament, the vial being movable relative to the housing. The container may further include a plunger associated with the proximal end of the vial, the plunger configured to slide within the vial from the proximal end to the distal end of the vial to dispel the medicament from the vial. The plunger may be associated with a plunger rod configured to interact with the plunger. The container may further include an injection member associated with the distal end of the vial, such that medicament dispelled from the vial passes through the injection member to the target location. A slidable interaction member is associated with the distal end of the vial, the slidable interaction member configured to slide with the vial; and a safety cap including a cap groove, the safety cap configured to interact with the distal end of the housing. Moving the vial toward the distal end of the housing causes the slidable interaction member to interact with the cap locking tab, biasing the cap locking tab outward, such that adjoining the safety cap to the distal end of the housing causes the cap groove to interact with the cap locking tab, preventing removal of the safety cap after use of the container.

The method further includes applying the distal end of the container to a target area on the subject and depressing the plunger rod to insert the injection member and deliver the medicament. In a further embodiment, the method may include releasing the plunger rod to allow retraction of the injection member, wherein upon retraction, the injection member is locked within the housing. In still a further embodiment, the method may include removing the safety cap prior to the applying step. In yet a further embodiment, the method may include attaching the safety cap subsequent to the releasing step, whereby the safety cap is permanently locked.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

A pictorial instruction for use (IFU) may be provided in non-limiting embodiments of the container 100 described herein. In one non-limiting embodiment, the pictorial IFU may include text, pictures, or other indicators and may be located on any portion of the container 100, 200, 300, 400. There may be one or more pictorial IFU's and the pictorial IFU may include audio in place of or in addition to visual pictorial IFU indicators, in non-limiting embodiments. In one non-limiting example, a pictorial IFU may include a series of light emission diodes (LEDs) on the plunger body in the shape of an arrow pointing downward indicating to a user to press the plunger toward the distal end of the housing 110, 210 in a first step, another pictorial IFU such as a series of LED's in the shape and color of a octagon to signal stop or wait to the user, to indicate that the injection is in process, and the medicament 122 is slowly being delivered to the target area, and not to remove the container 100, 200 from the target surface. Upon completion of medicament delivery to the target area, an upright green arrow shown in LEDs may be provided on the housing 110, 210, for example, indicating that removal of the container 100, 200 from the target surface is suggested. As aforementioned, the pictorial IFU may not be limited to the embodiments described herein. An LCD showing photos or video demonstrating, for example, use of the device may also be provided as a pictorial IFU. In other non-limiting embodiments, a combination of lights and sound may be used to guide a user by way of the pictorial IFU, for example. The location and type of pictorial IFU described herein are provided for example only, and are not intended to be limiting.

What is claimed is:

1. A container for delivering a medicament to a target location, the container comprising:
a housing comprising a proximal end and a distal end;
a vial comprising a proximal end and a distal end, the vial configured to contain the medicament, said vial configured to move relative to the housing;
an injection member associated with the distal end of the vial, such that the medicament delivered from the vial passes through the injection member to the target location;
a plunger slidable within the vial from the proximal end of the vial to the distal end of the vial to dispel the medicament from the vial;
a biasing member disposed within the housing;
at least one resistance feature associated with the container, the at least one resistance feature comprising at least one flexible tab;
a plunger rod extending into the housing, said plunger rod comprising a proximal end positioned external to the housing, and a distal end;
wherein the at least one flexible tab is associated with the plunger rod, wherein upon application of a force to the plunger rod, the at least one flexible tab directly contacts the vial to move the vial distally to eject the injection member, and upon reaching a threshold resistance force, the at least one flexible tab flexes inward, thereafter allowing the plunger rod to slide within the vial to deliver the medicament upon further force via the plunger rod, such that delivery of the injection member is complete prior to delivery of the medicament therethrough, and wherein following the delivery of the medicament, release of the force to the plunger rod causes release of the biasing member, such that the injection member and the vial are retracted into the housing; and
wherein the housing further comprises a cap locking tab and a slidable interaction member at the distal end of the housing, during use of the container, the distal movement of the vial causes the slidable interaction member to interface with the cap locking tab, biasing the cap locking tab outward, such that placement of a safety cap on a distal end of the container causes interaction between the safety cap and the cap locking tab, preventing subsequent removal of the safety cap.

2. The container of claim 1, further comprising a gap disposed between the plunger and the distal end of the plunger rod prior to the sliding of the plunger rod within the vial to deliver the medicament.

3. The container of claim 1, further comprising one or more plunger adaptors disposed between the at least one flexible tab and the proximal end of the vial.

4. The container of claim 1, wherein the plunger rod comprises a triangular body comprising a first surface, a second surface, and a third surface.

5. The container of claim 4, further comprising a visual indicator on at least one of the first surface, the second surface or the third surface of the plunger rod.

6. The container of claim 5, wherein the visual indicator provides a status of use of the container to a user of the container.

\* \* \* \* \*